US005635218A

United States Patent [19]

Prakash et al.

[11] Patent Number: 5,635,218

[45] Date of Patent: Jun. 3, 1997

[54] METHOD OF TREATING CANCER BY CONJUNCTIVE THERAPY WITH N,N'-BIS[3-(ETHYLAMINO)PROPYL]-1,7-HEPTANEDIAMINE AND A CYTOTOXIC AGENT

[75] Inventors: Nellikunja J. Prakash, Cincinnati; Terry L. Bowlin, Maineville, both of Ohio

[73] Assignee: Merrell Pharmaceuticals Inc., Cincinnati, Ohio

[21] Appl. No.: 460,017

[22] Filed: Jun. 2, 1995

Related U.S. Application Data

[62] Division of Ser. No. 437,469, May 9, 1995, Pat. No. 5,561,136, which is a continuation of Ser. No. 187,437, Jan. 26, 1994, abandoned, which is a continuation-in-part of Ser. No. 62,693, May 17, 1993, abandoned, which is a continuation of Ser. No. 985,515, Dec. 2, 1992, abandoned, which is a continuation of Ser. No. 863,526, Apr. 3, 1992, abandoned, which is a continuation of Ser. No. 626,814, Dec. 13, 1990, abandoned.

[51] Int. Cl.$^6$ .......................... A61K 33/24; A61K 31/28; A61K 31/13
[52] U.S. Cl. .......................... 424/649; 514/492; 514/674
[58] Field of Search .......................... 424/649; 514/492, 514/674

[56] References Cited

U.S. PATENT DOCUMENTS

| | | | |
|---|---|---|---|
| 4,048,324 | 9/1977 | Kohn | 424/294 |
| 4,719,313 | 1/1988 | Gerhart et al. | 514/672 |
| 5,109,024 | 4/1992 | Prakash et al. | 514/674 |

FOREIGN PATENT DOCUMENTS

| | | |
|---|---|---|
| 0277635 | 8/1985 | European Pat. Off. . |
| 0162413 | 11/1985 | European Pat. Off. . |
| 0270349 | 6/1988 | European Pat. Off. . |
| 0311068 | 4/1989 | European Pat. Off. . |
| 0378146 | 7/1990 | European Pat. Off. . |
| 0399519 | 11/1990 | European Pat. Off. . |

OTHER PUBLICATIONS

The Merck Index, 11th ED, 1989, Merck & Co, Inc., Rahway, N.J., pp. 276 and 361.
Hall, M. J., et al., J. Antimicrobial Chemotherapy, vol. 11, 427–433, 1983.
The Merck Index, 9th Edition, Merck & Co., Inc., Rahway, N.J., pp. 1281–1282, 1976.
Prakash, et al., Anticancer Research, vol. 10(5A):1281–1288 (Sep.–Oct. 1990).
Bergeron, R.J., Acc. Chem. Res., vol. 19, 105–113 (1986).
P. Calabresi et al., "Chemotherapy of Neoplastic Diseases", Goodman & Gillman's The Pharmaceutical Basis of Therapeutics, 8th Ed., pp. 1202–1263, (1990).

*Primary Examiner*—Jerome D. Goldberg
*Attorney, Agent, or Firm*—T. Helen Payne

[57] ABSTRACT

The present invention relates to a method of treating a patient suffering from a neoplastic disease state comprising administering to said patient an effective antineoplastic amount of N,N'-bis[3-(ethylamino)propyl]-1,7-heptanediamine in conjunctive therapy with an effective antineoplastic amount of a cytotoxic agent selected from the group consisting of an antineoplastic vinca alkaloid, an antineoplastic antibiotic, an antineoplastic antimetabolite and an antineoplastic platinum coordination complex, wherein a synergistic antineoplastic effect results.

12 Claims, No Drawings

METHOD OF TREATING CANCER BY CONJUNCTIVE THERAPY WITH N,N'-BIS[3-(ETHYLAMINO)PROPYL]-1,7-HEPTANEDIAMINE AND A CYTOTOXIC AGENT

CROSS-REFERENCE TO RELATED APPLICATION

This is a division of application Ser. No. 08/437,469, filed May 9, 1995, now U.S. Pat. No. 5,561,836, which is a continuation of application Ser. No. 08/187,437, filed Jan. 26, 1994, now abandoned, which is a continuation-in-part of application Ser. No. 08/062,693, filed May 17, 1993, now abandoned, which is a continuation of application Ser. No. 07/985,515, filed Dec. 2, 1992, now abandoned, which is a continuation of application Ser. No. 07/863,526, filed Apr. 3, 1992, now abandoned, which is a continuation of application Ser. No. 07/626,814, filed Dec. 13, 1990, now abandoned, which is herein incorporated by reference.

BACKGROUND OF THE INVENTION

Neoplastic disease states in humans are recognized throughout the world as being serious and oftentimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survivability of the patient, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states.

Certain vinca alkaloids, antibiotics, antimetabolites and platinum coordination complexes are well known as effective antineoplastic agents [See Calabresi, P., and Chabner, B. A., "CHEMOTHERAPY OF NEOPLASTIC DISEASES", Section XII, GOODMAN AND GILLMAN'S, THE PHARMACOLOGICAL BASIS OF THERAPEUTICS, 8th ed., 1990, Pergamon Press Inc., Elmsford, N.Y.]. For example, vinblastine and vincristine are vinca alkaloids which are useful antineoplastic agents. Taxol is another vinca alkaloid which has activity against malignant melanoma and carcinoma of the ovary. Antibiotics which possess antineoplastic properties include adriamycin (doxorubicin), dactinomycin (actinomycin D), daunorubicin (daunomycin, rubidomycin), bleomycin, plicamycin (mithramycin) and mitomycin (mitomycin C). Methotrexate, cytarabine (AraC), azauridine, azaribine, fluorodeoxyuridine, deoxycoformycin and mercaptopurine are examples of antimetabolites with antineoplastic properties. Cisplatin (cis-DDP) and carboplatin are platinum coordination complexes which are useful antineoplastic agents. These agents are proven to be useful in the treatment of patients suffering from a variety of neoplastic disease states.

Certain polyamine compounds, such as N,N'-bis[3-(ethylamino)propyl]-1,7-heptanediamine, are also well known as effective antineoplastic agents [European Patent Application Publication No. 0 378 146, published July 18, 1990, and European Patent Application Publication No. 0 311 068, published Apr. 12, 1989]. These polyamines are also useful in the treatment of patients suffering from a variety of neoplastic disease states.

It has now been found that in treating a patient afflicted with certain neoplastic disease states, conjunctive therapy with N,N'-bis[3-(ethylamino)propyl]-1,7-heptanediamine and a cytotoxic agent selected from the group consisting of an antineoplastic vinca alkaloid, an antineoplastic antibiotic, an antineoplastic antimetabolite and an antineoplastic platinum coordination complex, will provide a synergistic antineoplastic effect.

A synergistic effect is achieved when a greater antineoplastic effect results with a conjunctive therapy than use of either drug alone. One advantage of conjunctive therapy with a synergistic effect is that lower dosages of one or both of the drugs may be used so that the therapeutic index (Ti) is increased and toxic side effects are reduced.

SUMMARY OF THE INVENTION

The present invention provides a method of treating a patient suffering from a neoplastic disease state comprising administering to said patient an effective antineoplastic amount of N,N'-bis[3-(ethylamino)propyl]-1,7-heptanediamine in conjunctive therapy with an effective antineoplastic amount of a cytotoxic agent selected from the group consisting of an antineoplastic vinca alkaloid, an antineoplastic antibiotic, an antineoplastic antimetabolite and an antineoplastic platinum coordination complex, wherein a synergistic effect results.

More specifically, the present invention provides a method of treating a patient suffering from a neoplastic disease state comprising administering an effective antineoplastic amount of N,N'-bis[3-(ethylamino)propyl]-1,7-heptanediamine in conjunctive therapy with an effective antineoplastic amount of vinblastine, cisplatin, AraC or adriamycin.

DETAILED DESCRIPTION OF THE INVENTION

The polyamine N,N'-bis[3-(ethylamino)propyl]-1,7heptanediamine can be prepared as described in European Patent Application Publication No. 0 378 146, published Jul. 18, 1990, and European Patent Application Publication No. 0 311 068, published Apr. 12, 1989. In order to illustrate the preparation of N,N'-bis[3-(ethylamino)propyl]-1, 7heptanediamine, the following example is provided. The example is illustrative only and is not intended to limit the invention in any way. All temperatures are in degrees Celsius and the following abbreviations are used: (gm) is grams, (mol) is moles, (ml) is milliliters, (1) is liters, (lb/in$^2$) is pounds per square inch, (TLC) is thin layer chromatography, (THF) is tetrahydrofuran, (DMF) is dimethyl formamide, (mp) is melting point, (mm/Hg) is pressure expressed as millimeters of mercury, (bp) is boiling point, (N) is normal.

EXAMPLE 1

N,N'-Bis [3-(ethylamino) propyl]-1,7-heptanediamine

Steps A and B: 1,5,13,17-Tetraazaheptadecane tetrahydrochloride

Prepare the title compound by the method of Israel et al., J. Med. Chem. 7, 710 (1964).

Step C: 1,5,13,17-Tetra(t-butoxycarbonyl)-1,5,13,17-tetraazaheptadecane

Combine 1,5,13,17-tetraazaheptadecane tetrahydrochloride (3.9 gm, 0.01 mol) and sodium hydroxide (1.76 gm, 0.44 mol) in water (44 ml) and stir until homogeneous. To this mixture add di-t-butyldicarbonate (9.6 gm, 0.044 mol) in THF (88 ml) and stir for 3 hours. Dilute the mixture with ethyl acetate (EtOAc) [300 ml] and separate the organic layer. Dry the organic layer over anhydrous MgSO₄ and evaporate in vacuo to obtain a viscous oil. Purify the residue by flash chromatography (silica gel) eluting with 25% EtOAc/hexane to yield 3.0 gm of the title compound. $R_f$ is 0.20 on silica gel plates eluted with 25% EtOAc/hexane.

Step D: 3,7,15,19-Tetra(t-butoxycarbonyl) -3,7,15,19-tetraazaheptadecane

Combine 1,5,13,17-tetra(t-butoxycarbonyl)-1,5,13,17-tetraazaheptadecane (3.0 gm, 0.0046 mol) and sodium hydride (50% in oil) [0.45 gm, 0.011 mol] in DMF (9 ml) and stir the mixture until hydrogen evolution ceases. Add ethyl iodide (0.9 ml, 0.011 mol ) and stir the mixture for 18 hours. Evaporate the DMF in vacuo and partition the residue between ethyl acetate (600 ml) and water (200 ml). Separate the organic layer, dry the organic layer over anhydrous MgSO₄ and evaporate in vacuo. Purify the residue by flash chromatography (silica gel) eluting with 20% EtOAc/hexane to yield 1.68 gm of the title compound. $R_f$ is 0.5 on silica gel plates eluted with 25% EtOAc/hexane.

Step E: N,N'-Bis[3-(ethylamino)propyl]-1,7-heptanediamine

Treat 3,7,15,19-tetra(t-butoxycarbonyl)-3,7,15,19-tetraazaheptadecane (1.68 gm, 0.0024 mol) with HCl in methanol (50 ml, 1.0 N) and stir overnight. Filter the mixture and recrystallize the title compound from methanol/water (20:80, v/v) to yield 0.5 gm of the title compound. $R_f$ is 0.39 on silica gel plates eluted with 40% ammonia (concentrated) in methanol; mp 322°–23° C. with degradation.

The antineoplastic vinca alkaloids, such as vinblastine and vincristine, the antineoplastic antibiotics, such as adriamycin (doxorubicin), dactinomycin (actinomycin D), daunorubicin (daunomycin, rubidomycin), bleomycin, plicamycin (mithramycin) and mitomycin (mitomycin C), the antineoplastic antimetabolites, such as methotrexate, cytarabine (AraC), azauridine, azaribine, fluorodeoxyuridine, deoxycoformycin and mercaptopurine, and the antineoplastic platinum coordination complexes, such as cisplatin (cis-DDP) and carboplatin, are readily available and their use as antineoplastic agents is well known and appreciated in the art [For example, See Calabresi, P., and Chabner, B. A., "CHEMOTHERAPY OF NEOPLASTIC DISEASES", Section XII, GOODMAN AND GILLMAN'S, THE PHARMACOLOGICAL BASIS OF THERAPEUTICS, 8th ed., 1990, Pergamon Press Inc., Elmsford, N.Y.].

The present invention provides a method of treating a patient suffering from a neoplastic disease state comprising conjunctive therapy with an effective antineoplastic amount of N,N'-bis[3-(ethylamino)propyl]-1,7-heptanediamine and an effective antineoplastic amount of a cytotoxic agent selected from the group consisting of an antineoplastic vinca alkaloid, an antineoplastic antibiotic, an antineoplastic antimetabolite and an antineoplastic platinum coordination complex. This conjunctive therapy unexpectedly provides a synergistic antineoplastic effect.

A synergistic antineoplastic effect results when antineoplastic effect is greater as a result of conjunctive therapy over individual therapy of each drug. One measurement of synergy is the Fractional Inhibitory Concentration (FIC). FIC represents the IC$_{50}$ of a drug in combination divided by the IC$_{50}$ of the drug acting alone. For two interacting drugs, the sum of the FIC's of each of the treatments expresses the extent of the synergistic interation. The FIC may be computed for any point on the isobole (usually the most significant is computed) by the following calculation:

$$FIC = \left[ \frac{IC_{50}\ \text{Compound}\ A\ \text{combined}}{IC_{50}\ \text{Compound}\ A\ \text{Alone}} \right] +$$

$$\left[ \frac{IC_{50}\ \text{Compound}\ B\ \text{combined}}{IC_{50}\ \text{Compound}\ B\ \text{Alone}} \right]$$

Where FIC is less than 1, there is synergy between the two treatments. Where FIC is 1, there is no synergy (additive effect/ The smaller the value for FIC the greater the synergistic interaction.

As used herein, the term "FIC" refers to the Fractional Inhibitory Concentration. The FIC may be computed for any point on the isobole by the following calculation:

$$FIC = \left[ \frac{IC_{50}\ \text{Compound}\ A\ \text{combined}}{IC_{50}\ \text{Compound}\ A\ \text{Alone}} \right] +$$

$$\left[ \frac{IC_{50}\ \text{Compound}\ B\ \text{combined}}{IC_{50}\ \text{Compound}\ B\ \text{Alone}} \right]$$

It is preferred that the FIC value of conjunctive therapy is less than 0.9. It is more preferred that the FIC value of conjunctive therapy is less than 0.75. It is even more preferred that the FIC value of conjunctive therapy is less than 0.5.

As used herein, the term "patient" refers to a warm-blooded animal such as a mammal which is afflicted with a neoplastic disease state. It is understood that dogs, cats, rats, mice, horses, bovine cattle, sheep, and humans are examples of animals within the scope of the meaning of the term.

The term "neoplastic disease state" as used herein refers to an abnormal state or condition characterized by rapidly proliferating cell growth or neoplasm. Neoplastic disease states for which conjunctive therapy according to the present invention will be particularly useful include: Leukemias such as, but not limited to, acute lymphoblastic, chronic lymphocytic, acute myloblastic and chronic mylocytic; Carcinomas, such as, but not limited to, those of the cervix, oesophagus, stomach, small intestines, brain, colon and lungs; Sarcomas, such as, but not limited to, oesteroma, osteosarcoma, lepoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease. Of course, one skilled in the art will recognize that not every combination of conjunctive therapy according to the present invention will be equally effective against each of the neoplastic disease states. Selection of the most appropriate combination is within the ability of one of ordinary skill in the art and will depend on a variety of factors including assessment of results obtained in standard animal cancer models and the effectiveness of the individual agents as monotherapy in treating particular neoplastic disease states. Conjunctive therapy may result in lowered doses of one or more of the antineoplastic agents.

For example, conjunctive therapy with N,N'-bis[3-(ethylamino)propyl]-1,7-heptanediamine and vinblastine will be particularly effective in the treatment of a patient afflicted with leukemia, carcinoma, lymphoma or osteosarcoma. Conjunctive therapy with N,N'-bis[3-(ethylamino)propyl]-1,7-heptanediamine and cisplatin will be particularly effective in the treatment of a patient afflicted with carcinoma, testicular teratoma or ovarian carcinoma. Conjunctive therapy with N,N'-bis[3-(ethylamino)propyl]-1,7-heptanediamine and adriamycin will be particularly effective in the treatment of a patient afflicted with breast carcinoma, leukemia, lymphoma and ovarian carcinoma. Conjunctive therapy with N,N'-bis[3-(ethylamino)propyl]-1,7-heptanediamine and AraC will be particularly effective in the treatment of a patient afflicted with leukemia.

In effecting treatment of a patient afflicted with a neoplastic disease state as described above, the polyamine compound N,N'-bis[3-(ethylamino)propyl]-1,7-heptanediamine is administered in conjunctive therapy with a cytotoxic agent selected from the group consisting of an antineoplastic vinca alkaloid, an antineoplastic antibiotic, an antineoplastic antimetabolite and an antineoplastic platinum coordination complex. As used herein, the term "conjunctive therapy" contemplates co-administration of N,N'-bis[3-(ethylamino)propyl]-1,7-heptanediamine along with the cytotoxic agent. This co-administration may take place at essentially the same time, it may take place sequentially, or it may take place alternately.

In providing co-administration at essentially the same time, the courses of treatment with the polyamine and the selected cytotoxic agent run essentially concomitantly. In providing sequential co-administration, a full course of treatment of one of the agents is terminated and then followed by a full course of treatment of the other. In providing alternate co-administration, a partial course of treatment of one of the agents is terminated and then followed by a partial course of treatment of the other in an alternating manner until a full treatment of each agent is administered. When the polyamine compound and the selected cytotoxic agent are co-administered in a sequential or an alternate manner, it is generally preferred to administer the cytotoxic agent first and the polyamine compound last.

In effecting the conjunctive therapy according to the present invention, it is preferred to co-administer the polyamine compound and the selected cytotoxic agent in a sequential or an alternate manner. It is most preferred to co-administer the polyamine compound and the selected cytotoxic agent in a sequential manner.

As used herein, the term "effective antineoplastic amount" refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and does not necessarily indicate a total elimination of the neoplasm.

An effective antineoplastic amount of N,N'-bis[3-(ethylamino)propyl]-1,7-heptanediamine is expected to vary from about 10 milligram per kilogram of body weight per day (mg/kg/day) to about 100 mg/kg/day and preferably will be about 5 mg/kg/day to about 50 mg/kg/day.

The effective antineoplastic amounts of the various cytotoxic agents are well known and appreciated in the art. For example, an effective antineoplastic amount of vinblastine is expected to vary from about 3 mg/m$^2$/day to about 10 mg/m$^2$/day. An effective antineoplastic amount of cisplatin is expected to vary from about 20 mg/m$^2$/day to about 50 mg/m$^2$/day. An effective antineoplastic amount of adriamycin is expected to vary from about 60 mg/m$^2$/day to about 70 mg/m$^2$/day. An effective antineoplastic amount of AraC is expected to vary from about 1 mg/m$^2$/day to about 200 mg/m$^2$/day.

In effecting treatment of a patient afflicted with a disease state described above, N,N'-bis[3-(ethylamino) propyl]-1,7-heptanediamine can be administered in any form or mode which makes the compound bioavailable in effective amounts, including oral and parenteral routes. For example, in can be administered orally, subcutaneously, intraperitoneally, intramuscularly, intravenously, transdermally, intranasally, rectally, and the like. Oral administration is generally preferred. One skilled in the art of preparing formulations can readily select the proper form and mode of administration depending upon the particular circumstances, including the disease state to be treated, the stage of the disease, the form of administration of the selected cytotoxic agent, the manner of co-administration selected, and the like.

The compound N,N'-bis[3-(ethylamino) propyl]-1,7-heptanediamine can be administered alone or in the form of a pharmaceutical composition in combination with pharmaceutically acceptable carriers or excipients, the proportion and nature of which are determined by the solubility and chemical properties of N,N'-bis[3-(ethylamino) propyl]-1,7-heptanediamine, the chosen route of administration, and standard pharmaceutical practice. The compound N,N'-bis[3-(ethylamino) propyl]-1,7-heptanediamine, while effective itself, may be formulated and administered in the form of its pharmaceutically acceptable acid addition salt for purposes of stability, convenience of crystallization, increased solubility and the like.

The selected cytotoxic agent can be administered in a manner as is well known and accepted for the particular agent. For example, vinblastine, cisplatin, adriamycin and AraC are administered intravenously.

The following examples are provided in order to illustrate the method of use of the present invention. These examples are intended to be illustrative only and are not to be construed to limit the scope of the invention in any way.

EXAMPLE 2

Conjunctive Therapy in the Treatment of L1210 Leukemia in vivo

Groups of 5 mice (BDF1 male) were inoculated i.p. with $10^5$ L1210 leukemia cells on day 0. Vinblastine was administered i.p. at 0.5 mg/kg, i.p., on day 3. The compound N,N'-bis[3-(ethylamino) propyl]-1,7-heptanediamine was administered at 5 mg/Kg, every 3 hours, 4 times per day, on days 4 and 5. Control group received no treatment after inoculation. Relative survival time was determined and expressed as % T/C (mean survival time treated/mean survival time control×100). The results of these studies are presented in Table 1.

TABLE 1

| Antitumor Activity against L1210 Leukemia | | |
|---|---|---|
| Group | Dose, mg/Kg/day (Days Dosed) | Mean Survival Time (days ± S.D.[a]) |
| Control | — | 7.6 ± 0.5 |
| Vinblastine | 0.5 (day 3) | 10.0 ± 0.7 |
| 28,314[b] | 20 (days 4,5) | 12.6 ± 0.9 |
| Vinblastine + 28,314 | 20 (days 4,5) | 100% Cured[c] |

[a]S.D. = Standard Deviation
[b]28,314 = N,N'-Bis[3-(ethylamino)propyl]-1,7-heptanediamine
[c]Animals are considered cured if they survive beyond 45 days

EXAMPLE 3

Effect of Conjunctive Therapy in Mammalian Cell Culture MCA38 (mouse colon adenocarcinoma) and HeLa cells were grown in cell culture in the presence or absence of various concentrations of N,N'-Bis[3-(ethylamino)propyl]-1,7-heptanediamine (Compound 28,314), cisplatin, adriamycin, vinblastine and cytarabine (AraC) as indicated in Tables 2–9. Viablity of the cells after a 96 hour incubation was determined by a colorimetric assay, essentially as described by Carmichael et al. [Cancer Res. 47, 936 (1987)], whereby the cellular reduction of MTT [3-(4,5-dimethylthiazol-2-yl)-2,5-diphenyltetrozolium bromide]is measured.

$IC_{50}$ values were calculated for the individual treatments as well as for the combined treatments of Compound 28,314 with the various other agents. The $IC_{50}$ values at the various concentrations of test agents are presented in Tables 2–9.

In addition, the Fractional Inhibitory Concentration (FIC) for the various treatments was calculated. FIC's are an accepted measurement of synergy [Middleton and Westmacott, *J. Antimicrobial Chemother.* 11, 427 (1983)] and represents the $IC_{50}$ of a drug in combination divided by the $IC_{50}$ of the drug acting alone. For two interacting drugs, the sum of the FIC's of each of the treatments expresses the extent of the synergistic interaction. The FIC may be computed for any point on the isobole (usually the most significant is computed) by the following calculation:

$$FIC = [IC_{50}\ Compound\ A\ Combined/\ IC_{50}\ Compound\ A\ Alone] + [IC_{50}\ Compound\ B\ Combined/IC_{50}\ Compound\ B\ Alone].$$

Where FIC is less than 1, there is synergy between the two treatments, where FIC is 1, there is no synergy (additive effect). The smaller the value for FIC, the greater the synergistic interaction. The calculated values for FIC at the indicated concentrations are shown in Tables 2–9.

This data shows the synergistic antineoplastic effect of conjunctive therapy with Compound 28,314 and cytotoxic agents such as cisplatin, adriamycin, AraC, and vinblastine. However, in Table 7, a slight synergistic effect only was found for the conjunctive treatment of HeLa cells with Compound 28,314 and adriamycin.

TABLE 2

MCA 38 Cells Treated with Compound 20,114[a] and Cisplatin

| Concentration of 28,314 (µg/mL) | $IC_{50}$ (µg/mL) Cisplatin |
|---|---|
| 0 | 0.847 |
| 0.2 | 0.58 |
| 0.39 | 0.387 |
| 0.78 | 0.376 |
| 1.56 | 0.276 |
| 3.125* | 0.177* |
| 6.25 | 0.165 |
| 12.5 | 0.053 |
| 17.7[b] | 0 |
| *FIC | 0.39 (synergism) |

[a]28,314 = N,N'-Bis[3-(ethylamino)propyl]-1,7-heptanediamine
[b]$IC_{50}$ 28,314 alone

TABLE 3

MCA 38 Cells Treated with Compound 28,314[a] and Adriamycin

| Concentration of 28,314 (µg/mL) | $IC_{50}$ (µg/mL) Adriamycin |
|---|---|
| 0 | 0.0079 |
| 0.39 | 0.0075 |
| 0.78 | 0.0073 |
| 1.563 | 0.0070 |
| 3.125 | 0.0063 |
| 6.25* | 0.0025* |
| 12.5 | 0.0018 |
| 25[b] | 0 |
| *FIC | 0.57 (synergism) |

[a]28,314 = N,N'-Bis[3-(ethylamino)propyl]-1,7-heptanediamine
[b]$IC_{50}$ 28,314 alone

TABLE 4

MCA 38 Cells Treated with Compound 28,314[a] and AraC

| Concentration of 28,314 (µg/mL) | $IC_{50}$ (µg/mL) AraC |
|---|---|
| 0 | 0.66 |
| 0.1563 | 0.596 |
| 0.3125 | 0.488 |
| 0.625 | 0.36 |
| 1.25* | 0.23* |
| 2.5 | 0.071 |
| 3.54[b] | 0 |
| *FIC | 0.70 (synergism) |

[a]28,314 = N,N'-Bis[3-(ethylamino)propyl]-1,7-heptanediamine
[b]$IC_{50}$ 28,314 alone

TABLE 5

MCA 38 Cells Treated with Compound 28,314[a] and Vinblastine

| Concentration of 28,314 (µg/mL) | $IC_{50}$ (µg/mL) Vinblastin |
|---|---|
| 0 | 0.0595 |
| 0.1563 | 0.0548 |
| 0.3125 | 0.043 |
| 0.625 | 0.033 |
| 1.25* | 0.025* |
| 2.5 | 0.015 |
| 5.0 | 0.003 |
| 10.0[b] | 0 |
| *FIC | 0.55 (synergism) |

[a]28,314 = N,N'-Bis[3-(ethylamino)propyl]-1,7-heptanediamine
[b]$IC_{50}$ 28,314 alone

TABLE 6

HeLa Cells Treated with Compound 28,314[a] and Cisplatin

| Concentration of 28,314 (µg/mL) | $IC_{50}$ (µg/mL) Cisplatin |
|---|---|
| 0 | 0.359 |
| 0.39 | 0.336 |
| 0.78 | 0.276 |
| 1.563 | 0.186 |
| 3.125 | 0.130 |
| 6.25 | 0.088 |
| 12.5* | 0.074* |
| 25 | 0.068 |
| 50 | 0.068 |
| 100 | 0.057 |
| ~200[b] | 0 |
| *FIC | 0.27 (synergism) |

[a]28,314 = N,N'-Bis[3-(ethylamino)propyl]-1,7-heptanediamine
[b]$IC_{50}$ 28,314 alone

TABLE 7

HeLa Cells Treated with Compound 28,314[a] and Adriamycin

| Concentration of 28,314 (µg/mL) | $IC_{50}$ (µg/mL) Adriamycin |
|---|---|
| 0 | 0.0086 |
| 0.2 | 0.0067 |
| 0.39* | 0.0058* |
| 0.78 | 0.0048 |

TABLE 7-continued

HeLa Cells Treated with Compound 28,314[a] and Adriamycin

| Concentration of 28,314 (μg/mL) | $IC_{50}$ (μg/mL) Adriamycin |
|---|---|
| 1.5625 | 0.0015 |
| 1.59[b] | 0 |
| *FIC | 0.92 (slight synergism) |

[a]28,314 = N,N'-Bis[3-(ethylamino)propyl]-1,7-heptanediamine
[b]$IC_{50}$ 28,314 alone

TABLE 8

HeLa Cells Treated with Compound 28,314[a] and AraC

| Concentration of 28,314 (μg/mL) | $IC_{50}$ (μg/mL) AraC |
|---|---|
| 0 | 1.02 |
| 0.1563 | 0.63 |
| 0.3125 | 0.60 |
| 0.625 | 0.53 |
| 1.25 | 0.37 |
| 2.5 | 0.35 |
| 5 | 0.22 |
| 10* | 0.15* |
| 20 | 0.14 |
| 40 | 0.14 |
| 80 | 0.14 |
| ~160 | 0 |
| *FIC | 0.21 (synergism) |

[a]28,314 = N,N'-Bis[3-(ethylamino)propyl]-1,7-heptanediamine
[b]$IC_{50}$ 28,314 alone

TABLE 9

HeLa Cells Treated with Compound 28,314[a] and Vinblastine

| Concentration of 28,314 (μg/mL) | $IC_{50}$ (μg/mL) Vinblastin |
|---|---|
| 0 | 0.0016 |
| 0.1563 | 0.00133 |
| 0.3125 | 0.00133 |
| 0.625 | 0.00119 |
| 1.25 | 0.00117 |
| 2.5 | 0.00063 |
| 5* | 0.00024* |
| 10 | 0.00011 |
| 20 | 0.00009 |
| *FIC | 0.31 (synergism) |

[a]28,314 = N,N'-Bis[3-(ethylamino)propyl]-1,7-heptanediamine
[b]$IC_{50}$ 28,314 alone

What is claimed is:

1. A method of treating a patient suffering from a neoplastic disease state comprising administering to said patient an effective antineoplastic amount of N,N'-bis[3-(ethylamino) propyl]-1,7-hepanediamine and an antineoplastic platinum coordination complex selected from the group consisting of cisplatin and carboplatin wherein a synergistic antineoplastic effect results.

2. The method according to claim 1, wherein the antineoplastic disease state is carcinoma, testicular teratoma or ovarian carcinoma.

3. The method according to claim 1, wherein the antineoplastic disease state is a leukemia.

4. The method according to claim 1, wherein the antineoplastic disease state is a carcinoma.

5. The method according to claim 1, wherein the synergistic effect results in an FIC value of less than 1.

6. The method according to claim 5, wherein the synergistic effect results in an FIC value of less than 0.9.

7. The method according to claim 6, wherein the synergistic effect results in an FIC value of less than 0.75.

8. The method according to claim 7, wherein the synergistic effect results in an FIC value of less than 0.5.

9. The method according to claim 1, wherein administration is sequential.

10. The method according to claim 1, wherein administration is alternative.

11. The method according to claim 1, wherein the antineoplastic platinum coordination complex is cisplatin.

12. The method according to claim 11, wherein the antineoplastic disease state is carcinoma, testicular teratoma or ovarian carcinoma.

* * * * *

UNITED STATES PATENT AND TRADEMARK OFFICE
CERTIFICATE OF CORRECTION

PATENT NO. : 5,635,218

DATED : June 3, 1997

INVENTOR(s) : Nellikunja J. Prakash and Terry L. Bowlin

It is certified that error appears in the above-identified patent and that said Letters Patent is hereby corrected as shown below:

At column 1, line 65, the patent reads "potyamines" and should read --polyamines--.
At column 2, line 37, and again at column 2, line 42, the patent reads "7heptanediamine" and should read --7-heptanediamine--.
At column 3, line 7 and again at column 3, line 23, the patent reads "tetraazaheptadecane" and should read --tetraazaheneicosane--.
At column 7, line 35 in the Table 2 title, the patent reads "20,114$^a$" and should read --28,314$^a$--.

Signed and Sealed this

Sixteenth Day of June, 1998

*Attest:*

BRUCE LEHMAN

*Attesting Officer*   *Commissioner of Patents and Trademarks*